(12) United States Patent
Sapienza

(10) Patent No.: US 9,709,081 B2
(45) Date of Patent: Jul. 18, 2017

(54) FLUID TESTING DEVICE, AND A METHOD OF TESTING A PRESSURIZED FLUID FOR DISSOLVED AND/OR ENTRAINED GASSES

(71) Applicant: GM GLOBAL TECHNOLOGY OPERATIONS LLC, Detroit, MI (US)

(72) Inventor: Raymond J Sapienza, Fenton, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 128 days.

(21) Appl. No.: 14/880,570

(22) Filed: Oct. 12, 2015

(65) Prior Publication Data

US 2017/0102015 A1    Apr. 13, 2017

(51) Int. Cl.
| | | |
|---|---|---|
| *F15B 19/00* | (2006.01) | |
| *G01N 7/00* | (2006.01) | |
| *G01N 33/26* | (2006.01) | |

(52) U.S. Cl.
CPC .................... *F15B 19/00* (2013.01)

(58) Field of Classification Search
CPC ............ F15B 19/00; G01N 7/00; G01N 33/26
See application file for complete search history.

(56) References Cited

U.S. PATENT DOCUMENTS

| | | | | |
|---|---|---|---|---|
| 2,406,179 A * | 8/1946 | Walsh | ...................... | G01N 7/00 73/19.01 |
| 2,668,437 A * | 2/1954 | Patch | ...................... | G01N 7/00 73/1.61 |
| 3,521,478 A * | 7/1970 | Magorien | ................. | G01N 7/14 73/19.05 |
| 4,164,137 A * | 8/1979 | Williamson | ............. | G01N 1/14 73/19.1 |
| 4,341,534 A * | 7/1982 | Burger | ................... | F15B 21/044 95/260 |
| 5,243,848 A * | 9/1993 | Cox | ..................... | G01N 33/2841 73/19.05 |
| 5,621,161 A * | 4/1997 | Leyse | ..................... | G01N 27/06 73/19.01 |
| 7,559,223 B2 * | 7/2009 | Chen | ......................... | G01N 7/14 702/24 |
| 7,866,201 B1 * | 1/2011 | Tutu | ......................... | G01N 7/00 73/19.05 |

(Continued)

FOREIGN PATENT DOCUMENTS

FR          2572530 A1 *  5/1986   ............... G01N 7/00

*Primary Examiner* — Nguyen Ha
(74) *Attorney, Agent, or Firm* — Quinn IP Law

(57) ABSTRACT

A method of testing a pressurized liquid fluid for dissolved gasses includes evacuating both a first tank and a second tank. A test volume of a pressurized liquid fluid is introduced into the first tank. An initial absolute pressure in the second tank is sensed, and then fluid communication between the first tank and the second tank is opened to allow the pressurized fluid to flow from the first tank into the second tank, thereby de-pressurizing the fluid. The de-pressurized fluid in the second tank is maintained for a pre-defined out-gassing period, to allow any gasses in the de-pressurized fluid to separate from the de-pressurized fluid. A final absolute pressure in the second tank is sensed. A difference between the final absolute pressure and the initial absolute pressure is correlated to a volume of gasses released from the de-pressurized fluid.

20 Claims, 13 Drawing Sheets

(56) References Cited

U.S. PATENT DOCUMENTS

| | | | | |
|---|---|---|---|---|
| 8,490,464 B1* | 7/2013 | Selby | ............... | G01N 7/14 |
| | | | | 73/19.1 |
| 8,857,240 B2* | 10/2014 | Tastard | ............ | B01D 19/0036 |
| | | | | 141/94 |
| 2003/0029228 A1* | 2/2003 | Bloder | ............... | G01N 7/14 |
| | | | | 73/53.01 |
| 2003/0131652 A1* | 7/2003 | Chen | ............... | G01N 7/16 |
| | | | | 73/19.05 |

\* cited by examiner

FLUID TESTING DEVICE, AND A METHOD OF TESTING A PRESSURIZED FLUID FOR DISSOLVED AND/OR ENTRAINED GASSES

TECHNICAL FIELD

The disclosure generally relates to a fluid testing device, and to a method of testing a pressurized hydraulic liquid fluid for dissolved and entrained gasses with the fluid testing device.

BACKGROUND

Liquid fluids used in pressurized, hydraulic systems, should be absent of gasses, e.g., air, and/or water for optimal performance. Often, the hydraulic fluid will be processed prior to installation in the hydraulic system, in order to remove any gas and/or water contamination from the hydraulic fluid. The degree to which water is removed from the hydraulic fluid may be measured by an equilibrium reflux boiling point test. However, a test procedure for determining the degree to which gasses are removed from the liquid fluid, and particularly dissolved gasses, does not currently exist.

Entrained gasses in the hydraulic, liquid fluid, and particularly entrained air, may be detected through measurement of variation in density of the fluid by several methods or by visual inspection, and may appear as gas bubbles in the fluid. Entrained gasses in the liquid, hydraulic fluid, e.g., air bubbles in the fluid, negatively affect the performance of the hydraulic fluid in the hydraulic system due to the relative compressibility of the gas. Dissolved gasses in the hydraulic fluid are not visually detectable, and may not significantly affect the operation of the hydraulic fluid in the hydraulic system. However, a change in temperature and/or pressure of the fluid may cause any dissolved gasses in the hydraulic fluid to separate from the liquid hydraulic fluid, introducing entrained gasses into the hydraulic fluid, i.e., gas bubbles. Accordingly, it would be advantageous to be able to test the hydraulic fluid, at the condition (temperature/pressure) it may be delivered, with the gasses still in the dissolved state, in order to determine the degree to which gasses have been removed from the hydraulic fluid.

SUMMARY

A method of testing a pressurized fluid for dissolved and entrained gasses with a fluid testing device is provided. The fluid testing device includes a first tank having a first volume, and a second tank in fluid communication with the first tank and having a second volume. The second volume of the second tank is larger than the first volume of the first tank. The method includes connecting an evacuation and fluid filling system to the first tank, and evacuating both the first tank and the second tank with the evacuation and fluid filling system to form a vacuum in both the first tank and the second tank. Fluid communication between the first tank and the second tank is then blocked. A test volume of a pressurized fluid is introduced into the first tank, with the evacuation and fluid filling system. An initial absolute pressure in the second tank is sensed with an absolute pressure sensor. Fluid communication between the first tank and the second tank is then opened, to allow the test volume of the pressurized fluid to flow from the first tank into the second tank, and de-pressurize the fluid. The test volume of the de-pressurized fluid in the second tank is maintained for a pre-defined out-gassing period, to allow any dissolved or entrained gasses in the test volume of the previously pressurized fluid to separate from the liquid due to exposure to a deep vacuum. After the test volume of the now de-pressurized fluid has been maintained in the second tank for the pre-defined out-gassing period, a final absolute pressure in the second tank is sensed with the absolute pressure sensor. A difference between the final absolute pressure and the initial absolute pressure is correlated to a volume of gasses released from the test volume of the fluid.

A fluid testing device is also provided. The fluid testing device includes a first tank having a first inlet and a first outlet, and a fluid coupler attached to the first inlet. The fluid coupler is operable to connect the first inlet to an evacuation and fluid filling system. An inlet valve interconnects the first inlet and the fluid coupler. The inlet valve is operable to open fluid communication between the first inlet and the fluid coupler, and to also block fluid communication between the first inlet and the fluid coupler. A second tank includes a second inlet and a second outlet. The second inlet of the second tank is disposed in fluid communication with the first outlet of the first tank. A transfer valve interconnects the first outlet of the first tank and the second inlet of the second tank. The transfer valve is operable to open fluid communication between the first outlet and the second inlet, and to also block fluid communication between the first outlet and the second inlet. A drain valve is attached to the second outlet. The drain valve is operable to open fluid communication between the second outlet and atmospheric pressure, and to also block fluid communication between the second outlet and atmospheric pressure. An absolute pressure sensor is attached to the second tank. The absolute pressure sensor is operable to sense an absolute pressure within the second tank.

Accordingly, the fluid testing device enables the method of testing the pressurized fluid to determine an amount of dissolved gasses, e.g., air, in the pressurized fluid. The fluid testing device and method described herein enable a manufacturer to test and/or evaluate fluid processing techniques/processes for troubleshooting and/or quality performance purposes, which aid in the manufacturing processes utilizing the pressurized fluid.

The above features and advantages and other features and advantages of the present teachings are readily apparent from the following detailed description of the best modes for carrying out the teachings when taken in connection with the accompanying drawings.

DETAILED DESCRIPTION

Figure 1:
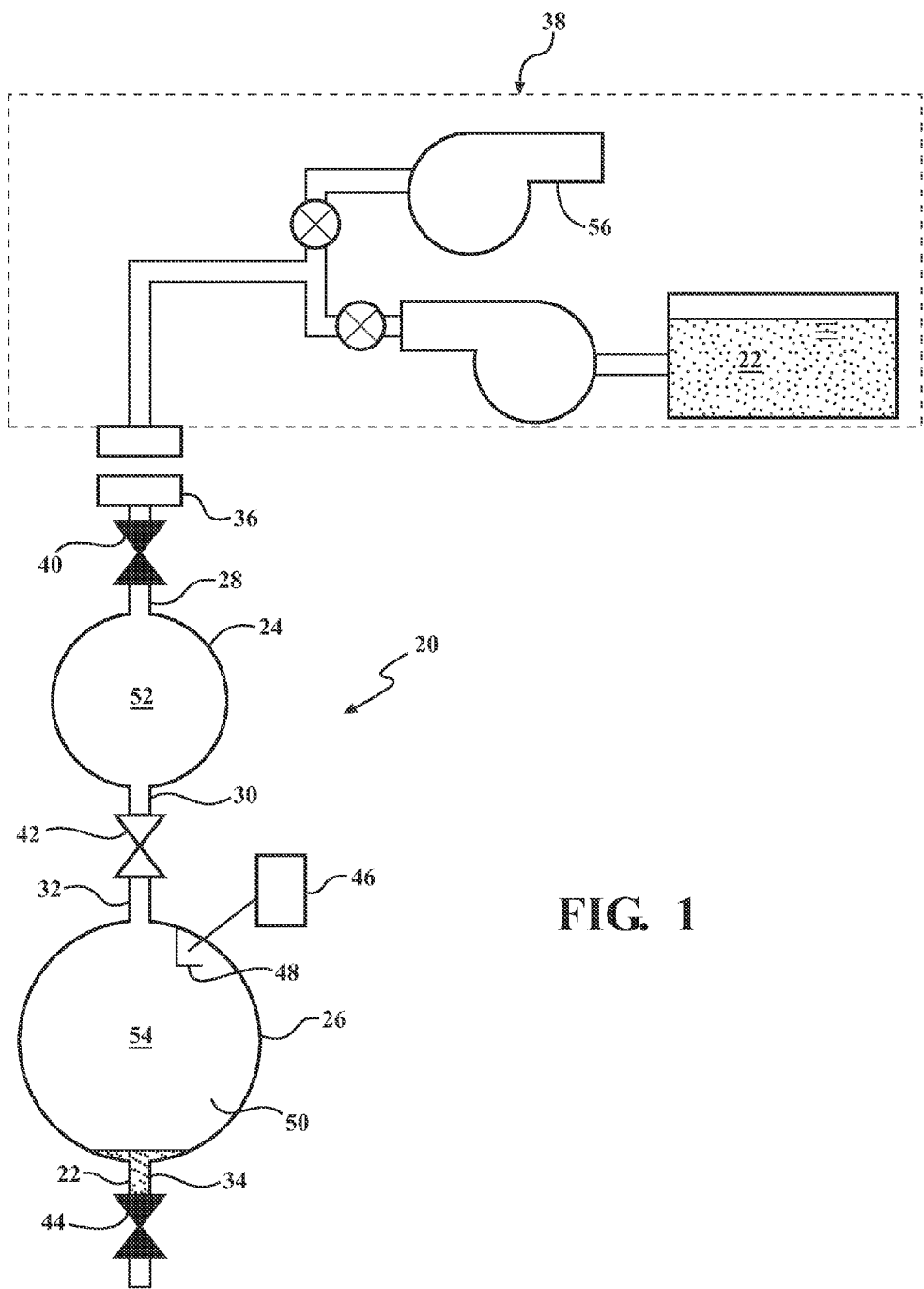
FIG. 1 is a schematic diagram of a fluid testing device, showing a storage position of a fluid testing device.

Those having ordinary skill in the art will recognize that terms such as "above," "below," "upward," "downward," "top," "bottom," etc., are used descriptively for the figures, and do not represent limitations on the scope of the disclosure, as defined by the appended claims.

Referring to the Figures, wherein like numerals indicate like parts throughout the several views, a fluid testing device is generally shown at 20. The fluid testing device 20 is operable to test a pressurized fluid 22 for dissolved and/or entrained gasses, such as but not limited to air. The pressurized fluid 22 includes a liquid, such as but is not limited to, a brake fluid, or some other liquid fluid intended for use in a hydraulic system. However, it should be appreciated that the fluid testing device 20 may be used to test any liquid fluid that is under pressure greater than atmospheric pressure, for a dissolved or entrained gas content. As used herein, the term "fluid" often, but not exclusively, refers to the liquid test sample proper, even though the term "fluid" may technically include a substance in either a liquid or a gas phase.

Referring to FIGS. 1 through 8, the fluid testing device 20 includes a first tank 24 and a second tank 26. The first tank 24 includes a first inlet 28, and a first outlet 30. The second tank 26 includes a second inlet 32, and a second outlet 34. As used herein, the terms "first" and "second" are used as adjectives to identify respective components and/or features of the fluid testing device 20, and are not intended to denote a relative quantity or number unless specifically noted herein. Accordingly, unless specifically noted herein, the terms "first" and "second" should not be interpreted to imply a number more than one.

The first tank 24 is disposed vertically above the second tank 26, i.e., the first tank 24 is disposed at a higher relative elevation than the second tank 26. The first inlet 28 is disposed at or near an upper vertical surface of the first tank 24, and the first outlet 30 is disposed at or near a lower vertical surface of the first tank 24. Accordingly, the first inlet 28 is disposed at a higher elevation than the first outlet 30. The second inlet 32 is disposed at or near an upper vertical surface of the second tank 26, and the second outlet 34 is disposed at or near a lower vertical surface of the second tank 26. Accordingly, the second inlet 32 is disposed at a higher elevation than the second outlet 34. This over/under or above/below configuration of the first tank 24 and the second tank 26, as described above, is needed in order to assure gravity assist in the complete transfer of the fluid 22 during the test process to assist the fluid motion which is provided by the pressure differential between the first tank 24 and the second tank 26 when hydraulic communication between the first tank 24 and the second tank 26 is enabled as a necessary part of the test process.

A fluid coupler 36 is attached to and disposed in fluid communication with the first inlet 28. The fluid coupler 36 is operable to connect the first inlet 28 to an evacuation and fluid filling system 38. The evacuation and fluid filling system 38 may include any system that is capable of evacuating a closed volume to form a vacuum therein, and supplying the pressurized fluid 22 under pressure into the closed volume after the closed volume has been evacuated. The evacuation and fluid filling system 38 supplies the fluid at a pressure that is greater than atmospheric pressure. Evacuation and fluid filling systems 38 are common in manufacturing processes and known to those skilled in the art. As such, the specific configuration and/or operation of the evacuation and fluid filling system 38 is not described in detail herein. The fluid coupler 36 may include any coupler capable of connecting to the evacuation and fluid filling system 38, and maintaining both a gas and liquid tight seal. For example, if the evacuation and fluid filling system 38 is configured for supplying a brake fluid to a vehicle during maintenance or manufacture of the vehicle, then the fluid coupler 36 may include an opening with specific geometric dimension that may be common to a vehicular brake master cylinder opening detail, such as known to those skilled in the art. However, it should be appreciated that the fluid coupler 36 may be configured in any suitable manner, and is not limited to any specific embodiment.

The fluid testing device 20 includes an inlet valve 40, which interconnects the first inlet 28 and the fluid coupler 36 to control fluid flow between the fluid coupler 36 and the first tank 24. The inlet valve 40 is operable or controllable between an open position and a closed position. When disposed in the open position, the inlet valve 40 allows or opens fluid communication between the first inlet 28 of the first tank 24 and the fluid coupler 36 to allow fluid flow between the first tank 24 and the fluid coupler 36. When disposed in the closed position, the inlet valve 40 does not allow or closes fluid communication between the first inlet 28 of the first tank 24 and the fluid coupler 36, to prevent fluid flow between the first tank 24 and the fluid coupler 36. The inlet valve 40 may include any style and/or configuration of valve capable of moving between the open position and the closed position described above, as long as such valve provides fluid isolation (both gas and liquid) of the testing device internal passages from outside atmospheric conditions. In other words, the inlet valve 40 must not leak externally at the pressures used in the test process. For example, the inlet valve 40 may include, but is not limited to, a ball valve, a gate valve, or some other similar control valve. The inlet valve 40 may be manually operated between the open position and the closed position, or may be controlled by an electronic, computer controller.

The second inlet 32 of the second tank 26 is disposed in fluid communication with the first outlet 30 of the first tank 24. The first outlet 30 of the first tank 24 is disposed vertically above the second inlet 32 of the second tank 26.

Accordingly, the first outlet 30 of the first tank 24 is disposed at a higher relative elevation than the second inlet 32 of the second tank 26.

A transfer valve 42 interconnects the first outlet 30 of the first tank 24 and the second inlet 32 of the second tank 26, to control fluid flow between the first tank 24 and the second tank 26. The transfer valve 42 is operable or controllable between an open position and a closed position. When disposed in the open position, the transfer valve 42 allows or opens fluid communication between the first outlet 30 of the first tank 24 and the second inlet 32 of the second tank 26 to allow fluid flow between the first tank 24 and the second tank 26. When disposed in the closed position, the transfer valve 42 does not allow or closes fluid communication between the first outlet 30 of the first tank 24 and the second inlet 32 of the second tank 26, to prevent fluid flow between the first tank 24 and the second tank 26. The transfer valve 42 may include any style and/or configuration of valve capable of moving between the open position and the closed position described above. For example, the transfer valve 42 may include, but is not limited to, a ball valve, a gate valve, or some other similar control valve. The transfer valve 42 may be manually operated between the open position and the closed position, or may be controlled by an electronic, computer controller.

A drain valve 44 is attached to the second outlet 34 of the second tank 26 for controlling fluid flow through the second outlet 34. The drain valve 44 is operable or controllable between an open position and a closed position. When disposed in the open position, the drain valve 44 allows or opens fluid communication between the second outlet 34 of the second tank 26 and atmosphere to drain fluid from the second tank 26. When disposed in the closed position, the drain valve 44 does not allow or closes fluid communication between the second outlet 34 of the second tank 26 and the outside atmosphere, to prevent fluid from draining from the tank. The drain valve 44 may include any style and/or configuration of valve capable of moving between the open position and the closed position described above. For example, the drain valve 44 may include, but is not limited to, a ball valve, a gate valve, or some other similar control valve. The drain valve 44 may be manually operated between the open position and the closed position, or may be controlled by an electronic, computer controller.

The second tank 26 includes an absolute pressure sensor 46. The absolute pressure sensor 46 is operable to sense an absolute pressure within the second tank 26. Preferably, the absolute pressure sensor 46 includes a digital sensor, and be coupled to and in communication with a computer or other similar electronic controller. However, it should be appreciated that the absolute pressure sensor 46 is not required to include a digital sensor. The absolute pressure sensor 46 measures pressure relative to a perfect vacuum. A "perfect vacuum" is defined herein as a volume or region containing no matter. Because all pressure readings from the absolute pressure sensor 46 are relative to a perfect vacuum, all pressure readings are always a positive number. The fluid testing device 20 uses the absolute pressure sensor 46 to prevent fluctuations in pressure measurement caused by variation in atmospheric pressure.

As shown in the Figures, the absolute pressure sensor 46 is directly attached to the second tank 26 via a dedicated port. The fluid testing device 20 may further includes a baffle 48 disposed within an interior 50 of the second tank 26. The baffle 48 is positioned to shield a probe or tip of the absolute pressure sensor 46 that may extend into the interior 50 of the second tank 26. The baffle 48 may be configured in any manner capable of shielding probe of the absolute pressure sensor 46, while still allowing the absolute pressure sensor 46 to sense the absolute pressure within the second tank 26. Alternatively, the absolute pressure sensor 46 may be attached to the second tank through one or more pipe fittings interconnecting the transfer valve 42 and the second inlet 32 of the second tank 26. Such a configuration may include a protective valve disposed between the second inlet 32 and the absolute pressure sensor 46 to protect the absolute pressure sensor from high fluid pressures during fluid transfer between the first tank 24 and the second tank 26.

The first tank 24 defines a first volume 52, and the second tank 26 defines a second volume 54. The second volume 54 of the second tank 26 is larger than the first volume 52 of the first tank 24. The reason and importance of having the second tank 26 larger than the first tank 24 is described in greater detail below. In an exemplary embodiment, the second volume 54 may be between 2% and 50% larger than the first volume 52, and more specifically, the second volume 54 may be between 5% and 15% larger than the first volume 52. The first volume 52 and the second volume 54 may each include a volume between 200 cc and 3000 cc. However, it should be appreciated that the relative size between the first volume 52 and the second volume 54, as well as the absolute sizes of the first volume 52 and the second volume 54, may differ from the exemplary sizes and ranges provided herein.

A method of testing a pressurized fluid 22 for dissolved and/or entrained gasses, with the fluid testing, is described below. As noted above, an exemplary use for the fluid testing device 20 and method described herein may include testing brake fluid from an evacuation and brake fluid filling system used to fill a hydraulic brake system of vehicles being manufactured in an automotive assembly plant. However, it should be appreciated that the test procedure may be used for other fluids intended for other applications.

As shown in the Figures, a closed valve is indicated by a solid or filled valve symbol, whereas an open valve is indicated by non-solid or non-filled valve symbol. The fluid being tested is generally indicate by the stippling pattern, and identified by reference numeral 22.

Referring to FIG. 1, the test procedure begins with the fluid testing device 20 disposed in a storage position, shown in FIG. 1, in which the inlet valve 40 and the drain valve 44 are disposed in their respective closed positions, and the transfer valve 42 is disposed in its respective open position. This storage position allows residual fluid from the previous test to drain from the first tank 24 into the second tank 26 (and subsequently be drained out of the drain valve 44 prior to beginning the next test) and also to prevent continuous exposure of the internals of the fluid testing device 20 to the atmosphere which would potentially allow atmospheric moisture to be absorbed by the residual fluid in the fluid testing device 20 (the test fluid potentially being hydrophilic, such as brake fluid). Moisture inside of the fluid testing device 20 may interfere with test results and is not desired. Any moisture inside of the fluid testing device should be purged as part of the test process. Keeping the fluid testing device 20 in the storage position limits atmospheric moisture from collecting within the fluid testing device 20, thereby reducing the time required to purge any moisture in the fluid testing device 20 prior to the next test process.

Figure 2:
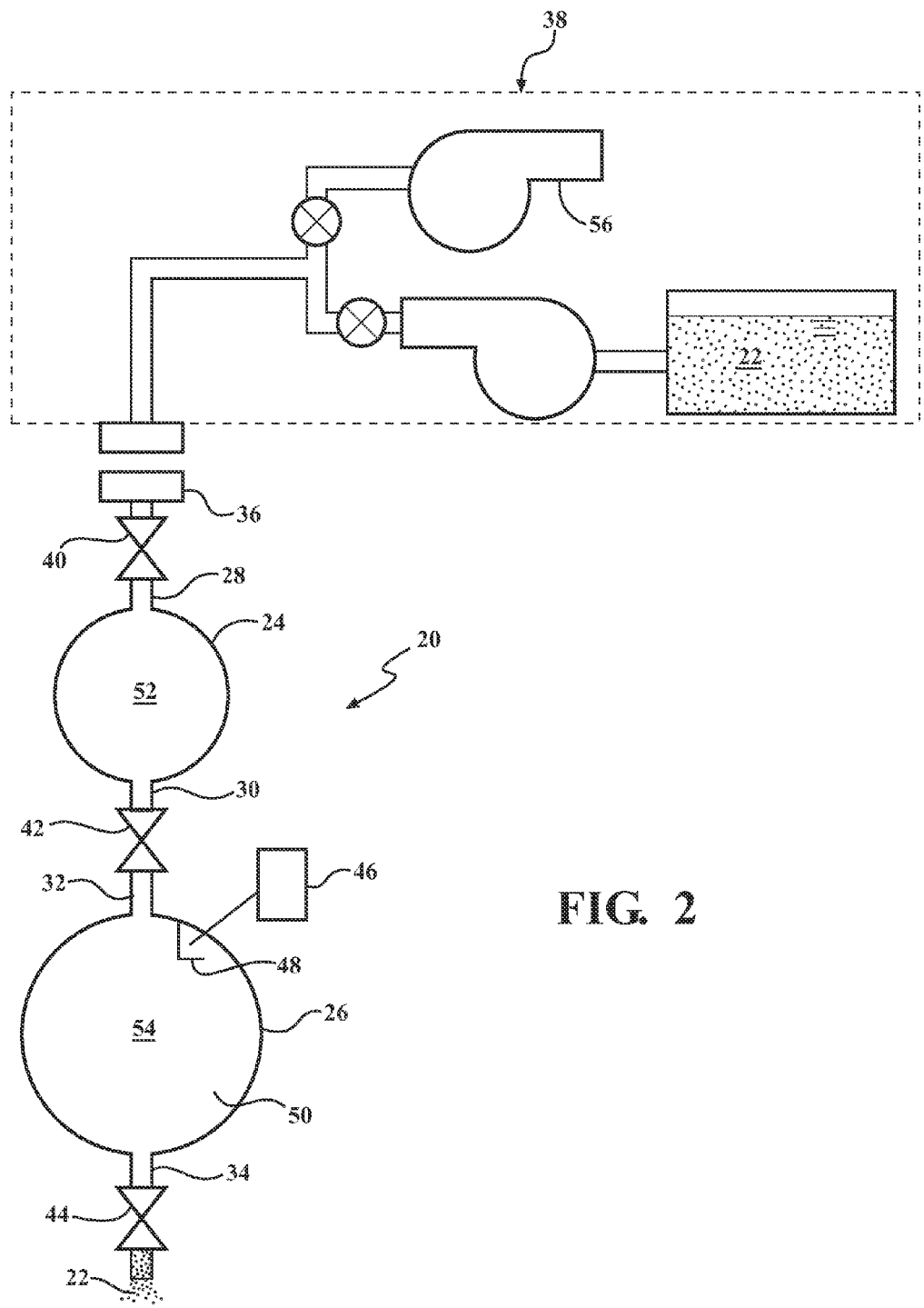
FIG. 2 is a schematic diagram of the fluid testing device, showing residual fluid within the fluid testing device being drained.

Referring to FIG. 2, prior to beginning the test proper, a preparatory step is required. Assuming the fluid testing device is stored in the storage position, in which the inlet valve 40 and the drain valve 44 are closed, and the transfer valve 42 is open, then the preparatory step includes briefly opening the inlet valve 40 and the drain valve 44 to allow any residual fluid to drain out of the fluid testing device 20. The drain valve 44 is maintained open until any residual fluid stops dripping from the second outlet 34 of the second tank 26. Once any residual fluid has drained out of the fluid testing device 20, the fluid testing device 20 is re-positioned into an initial test position, shown in FIG. 3 in which the inlet valve 40 and the transfer valve 42 are disposed in their respective open positions, and the drain valve is disposed in its respective closed position.

Figure 3:
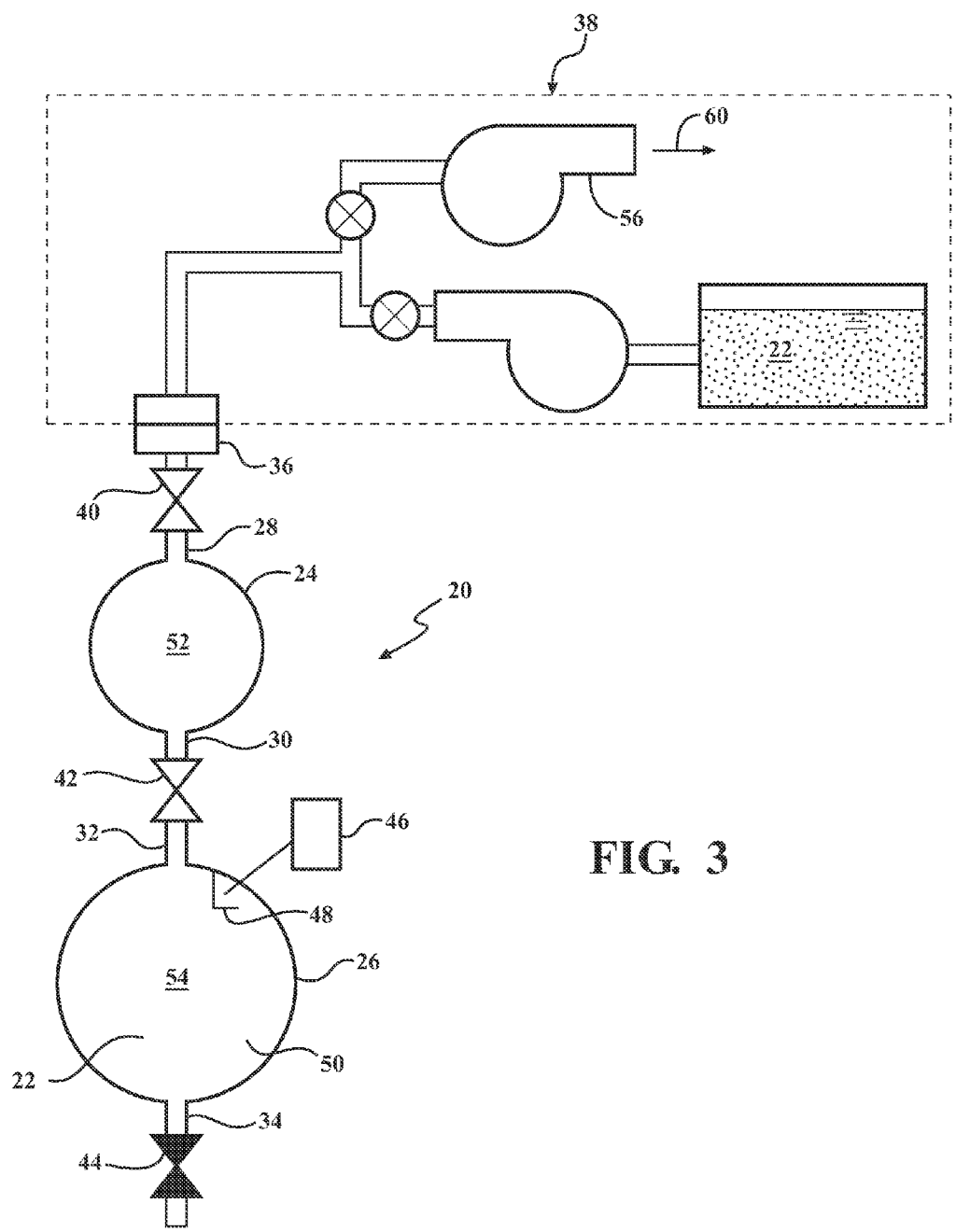
FIG. 3 is a schematic diagram of the fluid testing device, showing an initial test position for a method of testing a pressurized fluid for dissolved gasses.

Referring to FIG. 3, the start of the test proper includes connecting the evacuation and fluid filling system 38 to the first tank 24. As noted above, the evacuation and fluid filling system 38 is capable of forming a vacuum in a closed system/container, and also introducing or supplying a fluid under pressure to the closed system after the vacuum has been formed. Connecting the evacuation and fluid filling system 38 to the first tank 24 includes attaching or coupling the evacuation and fluid filling system 38 to the fluid testing device 20 with the fluid coupler 36, as described above.

After connection of the evacuation and fluid filling system 38 to the fluid coupler 36, the evacuation and fluid filling system 38 may be engaged to evacuate both the first tank 24 and the second tank 26 to form a vacuum in both the first tank 24 and the second tank 26. For example, a vacuum pump 56 of the evacuation and fluid filling system 38 may be actuated to pump air from the first tank 24 and the second tank 26 to form a vacuum therein. The removal of air from the fluid testing device 20 is generally shown by the flow arrow 60. It should be appreciated that because the transfer valve 42 begins the test procedure in its respective open position, the first tank 24 and the second tank 26 are in fluid communication with each other. As such, as the vacuum pump 56 draws air from the first tank 24, the vacuum pump 56 is simultaneously drawing air from the second tank 26 to form a vacuum in each of the first tank 24 and the second tank 26.

Figure 4A:
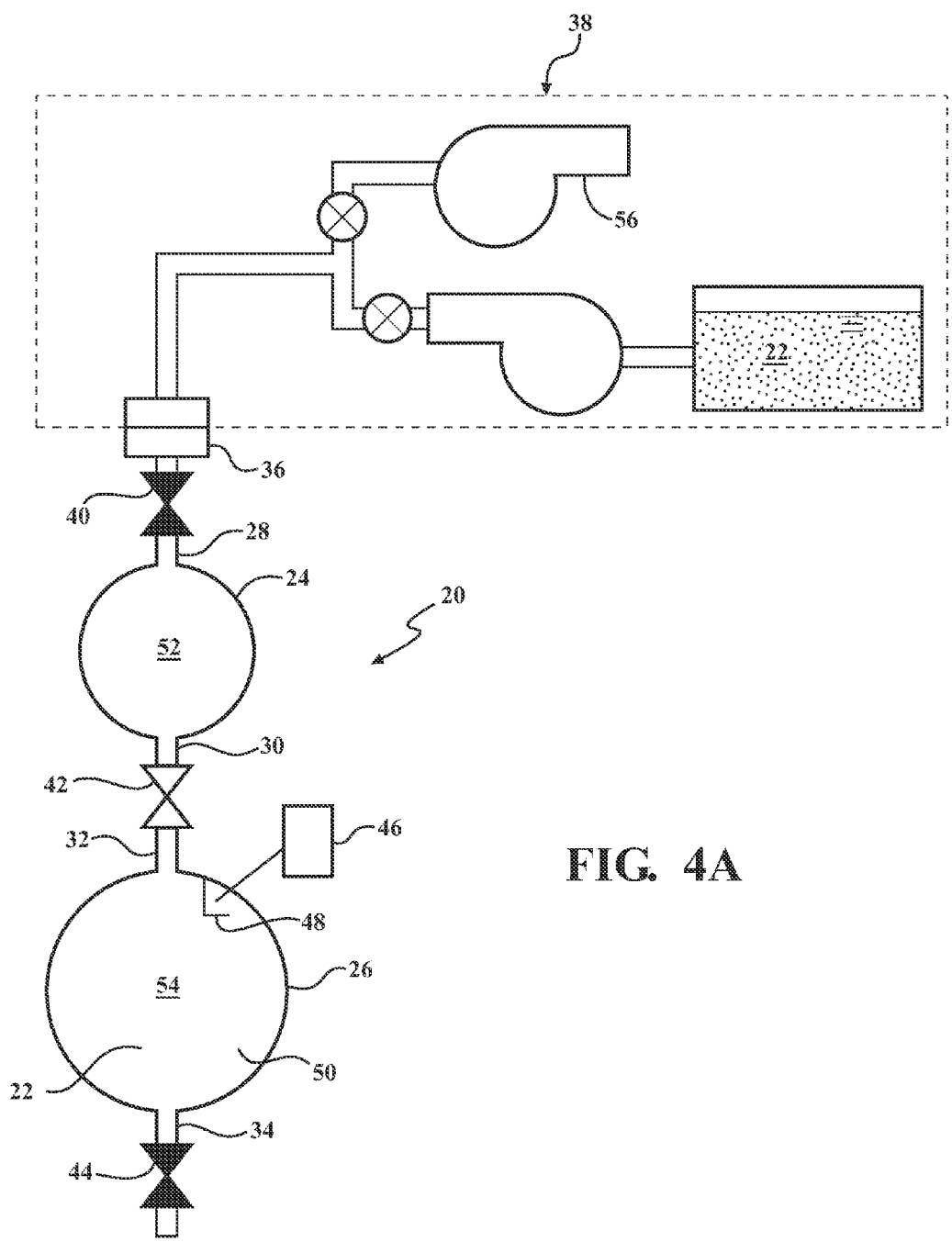
FIG. 4A is a schematic diagram of the fluid testing device shown coupled to a fluid evacuation and filling system for evacuating the fluid testing device.

After evacuating the first tank 24 and the second tank 26, and a vacuum has been formed in the first tank 24 and the second tank 26, the vacuum in both the first tank 24 and the second tank 26 may be maintained for a pre-defined vacuum soak period to remove moisture and/or any dissolved gasses from the residual fluid in the fluid testing device 20 which may interfere with the test results if not removed prior to the test. The process shall be hereafter referred to as "pre-test outgassing". The pre-defined vacuum soak period may be between 5 and 30 minutes, or as needed until the pre-test outgassing process is complete. After the pre-determined soak time, during which the vacuum pump 56 of the fluid evacuation and filling system 38 is providing the vacuum, fluid communication between the evacuation and fluid filling system 38 and the first tank 24 is closed by moving the inlet valve 40 into its respective closed position, such as shown in FIG. 4A.

Figure 4B:
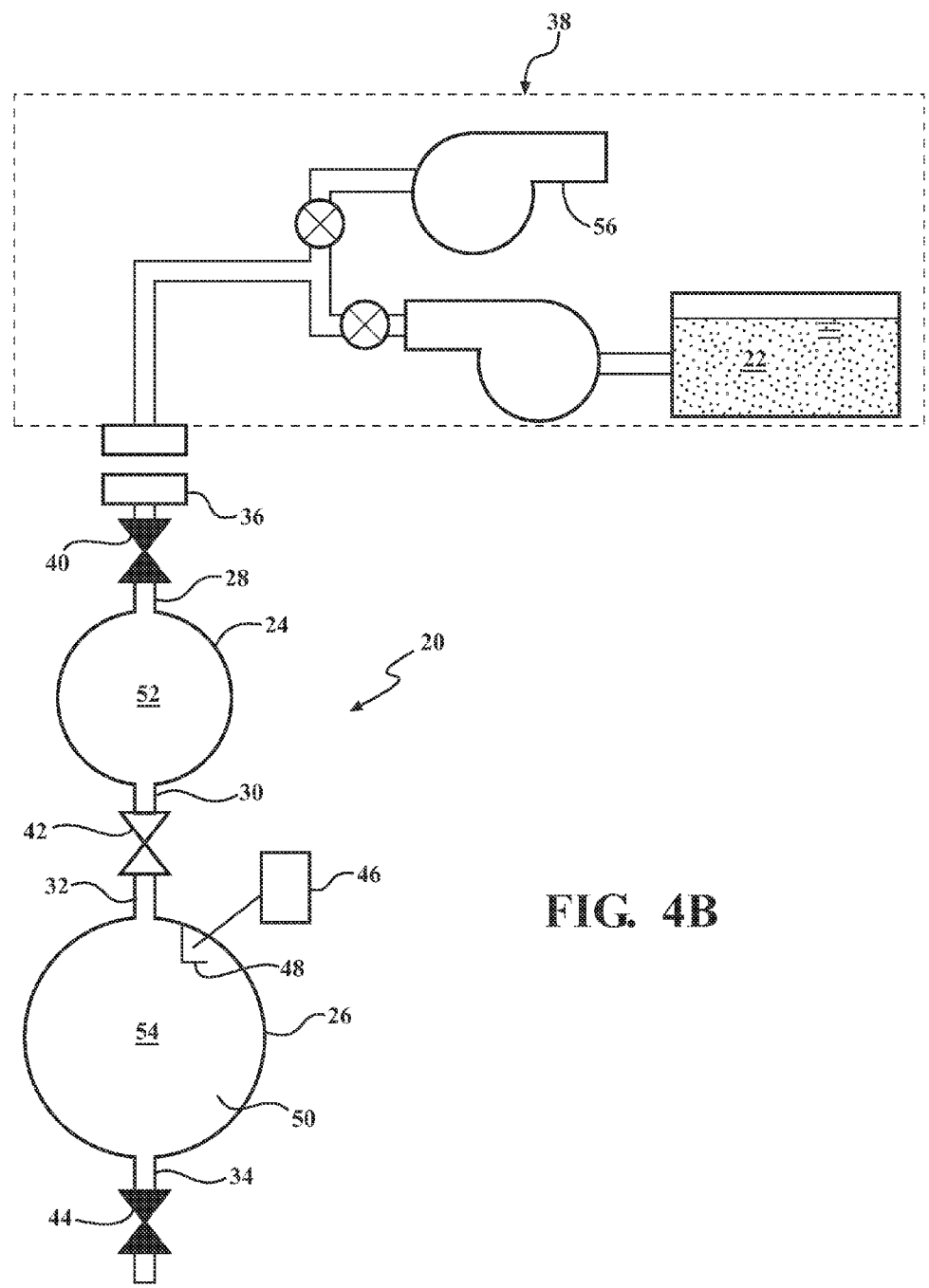
FIG. 4B is a schematic diagram of the fluid testing device shown de-coupled from the fluid evacuation and filling system for a vacuum decay test.

Referring to FIG. 4B, once the first tank 24 and the second tank 26 have been drawn down to a deep vacuum, and fluid communication between the evacuation and fluid filling system 38 has been closed, the fluid evacuation and filling system 38 is disconnected from the fluid testing device 20 for a pre-defined vacuum soak period, to test for leakage through either the inlet valve 40 or the drain valve 44. The pre-defined vacuum soak period may include any desirable period of time suitable for testing for leaks in the fluid testing device 20. For example, the pre-defined soak period may include a time of between 5 minutes and 30 minutes. It should be appreciated that a longer vacuum soak period will provide a more accurate test of the ability of the fluid testing device 20 to maintain the vacuum and assurance of proper outgassing.

While the fluid testing device 20 is isolated from the fluid evacuation and filling system 38, with the first tank 24 and the second tank 26 at a deep vacuum, the absolute pressure sensor 46 is monitored in order to test for sufficient outgassing of the residual fluid and to assure there are no leaks in the fluid testing device 20. If the pressure level in the first tank 24 and the second tank 26, as measured by the pressure sensor 46, is shown to rise at this point, additional outgassing time may be needed to more completely remove any moisture and/or dissolved gasses in the residual fluid in the fluid testing device 20, or leaks in the fluid testing device 20 may need to be found and repaired prior to proceeding with the test procedure. This test for a rise in pressure shall be subsequently referred to as the "vacuum decay check". Additional outgassing, if needed, is provided by once again connecting the fluid evacuation and filling system 30 to the fluid testing device 20, engaging the vacuum pump 56, and opening the inlet valve 40 for some period of time.

If the absolute pressure reading from the fluid testing device 20 does not change significantly during the vacuum decay check, then the fluid testing device 20 remains sealed, and the test process may be continued. However, if the absolute pressure reading from the fluid testing device 20 does change during the vacuum decay check, then the fluid testing device 20 is not operating properly, and the test procedure should be stopped. If there is no significant loss of the deep vacuum in the fluid testing device 20, the pre-test vacuum decay check is considered passed and the process continues. A significant loss of the deep vacuum is indicated by a pressure increase greater than 0.1 torr per second.

Figure 4C:
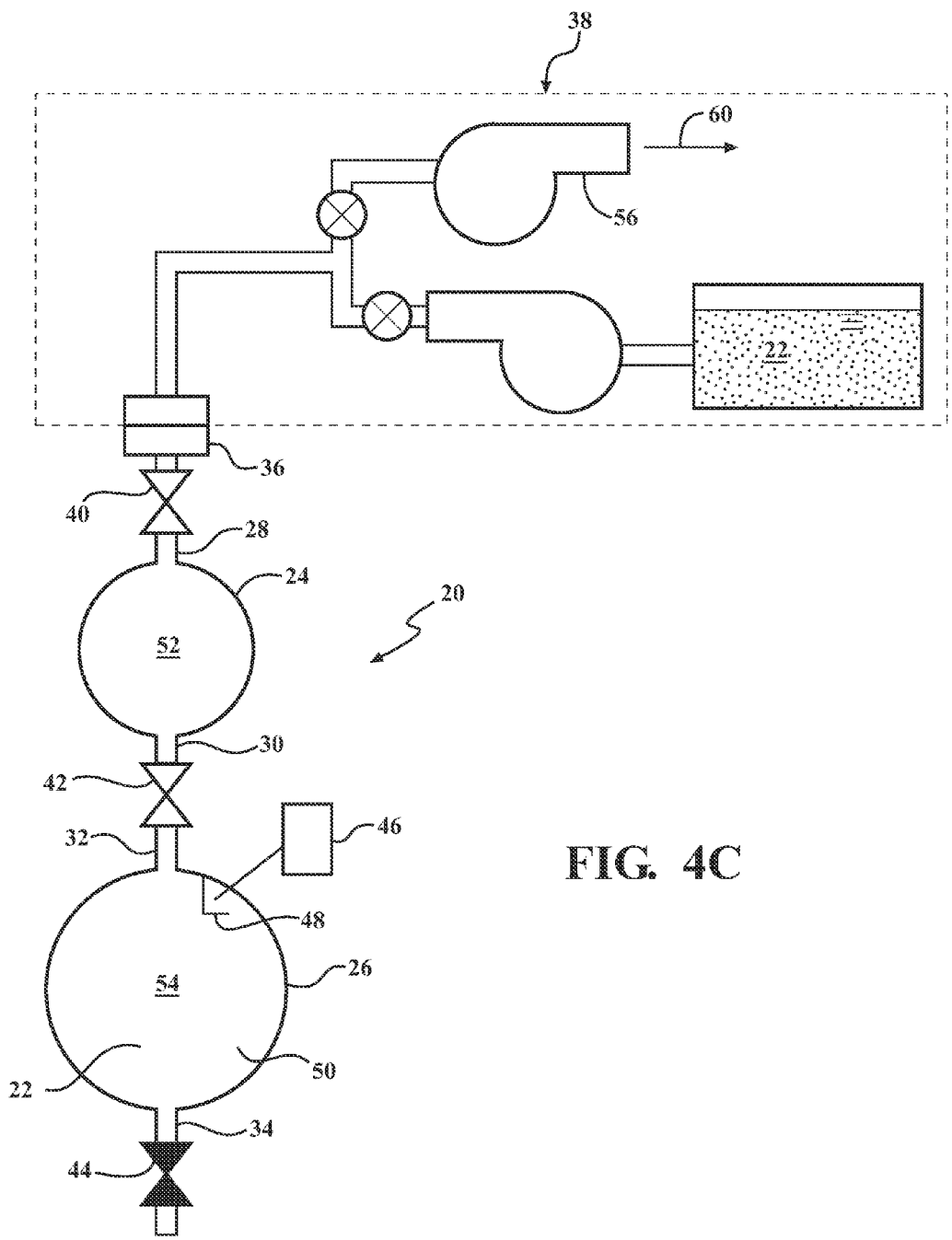
FIG. 4C is a schematic diagram of the fluid testing device shown coupled to the fluid evacuation and filling system for re-applying a deep vacuum to the fluid testing device.

Referring to FIG. 4C, after the vacuum in the first tank 24 and the second tank 26 has been maintained for the pre-defined vacuum soak period, and assuming the fluid testing device 20 has maintained the vacuum within the first tank 24 and the second tank 26, and the fluid testing device 20 is deemed to be operating properly, then the fluid evacuation and filling system 38 is re-connected to the fluid testing device 20, and a vacuum is re-applied to the fluid testing device 20 to bring both the first tank 24 and the second tank 26 back down to as deep of a vacuum level as possible in case there was any minor loss of vacuum inside the fluid testing device 20 during the vacuum decay check. The re-application of vacuum also clears the air from the interface between the evacuation and filling system 38 and the fluid coupler 36 to avoid air exposure to the fluid 22 when it is provided to the fluid testing device 20 later in the test process via this same pathway.

Figure 4D:
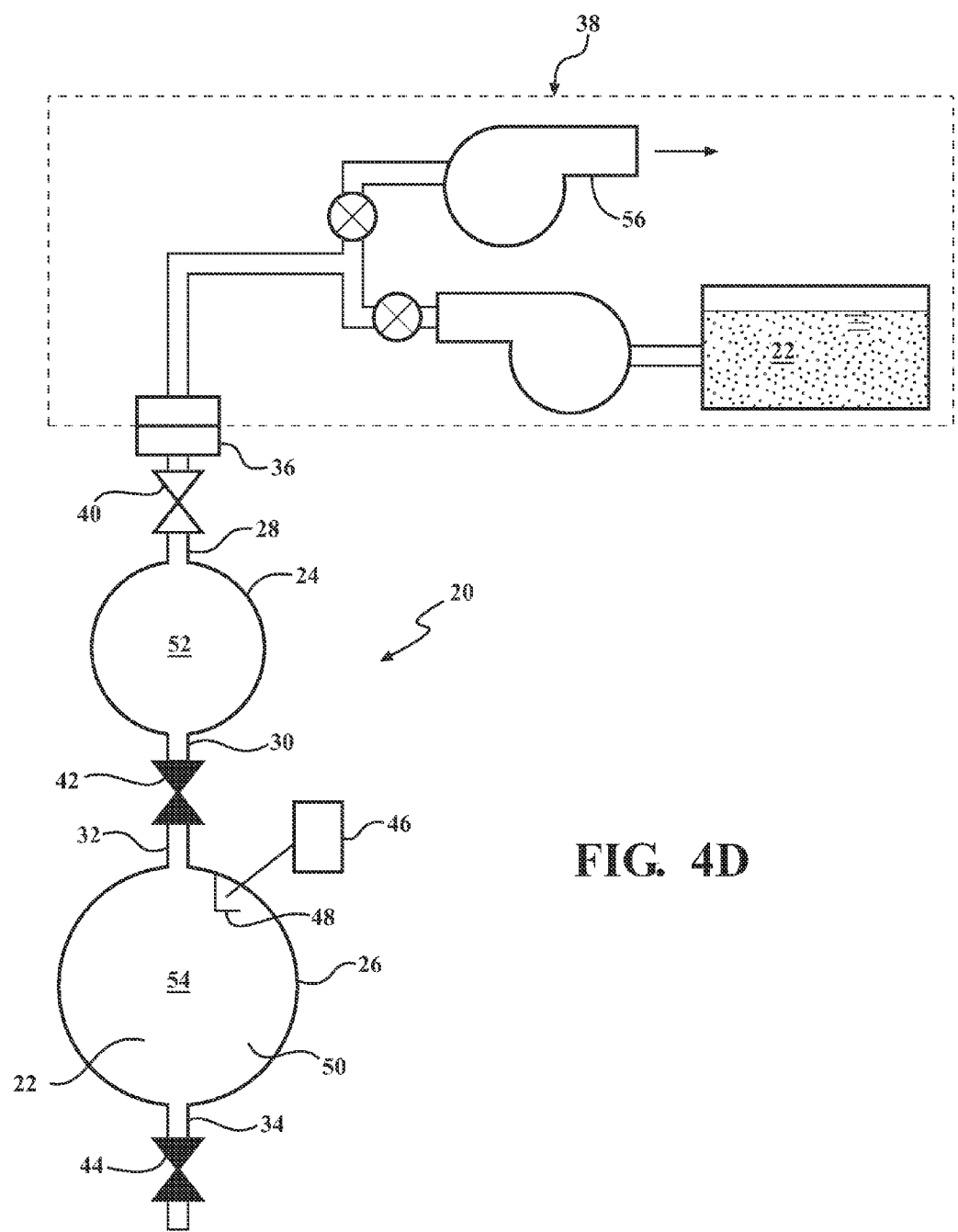
FIG. 4D is a schematic diagram of the fluid testing device showing a first tank being isolated from a second tank, while both in a deep vacuum.

Referring to FIG. 4D, once the first tank 24 and the second tank 26 have been brought down to the deepest possible vacuum by the vacuum pump 56, then fluid communication between the first tank 24 and the second tank 26 is closed. Fluid communication between the first tank 24 and the second tank 26 is closed by moving the transfer valve 42 into its respective closed position, thereby preventing fluid communication between the first tank 24 and the second tank 26.

Figure 5A:
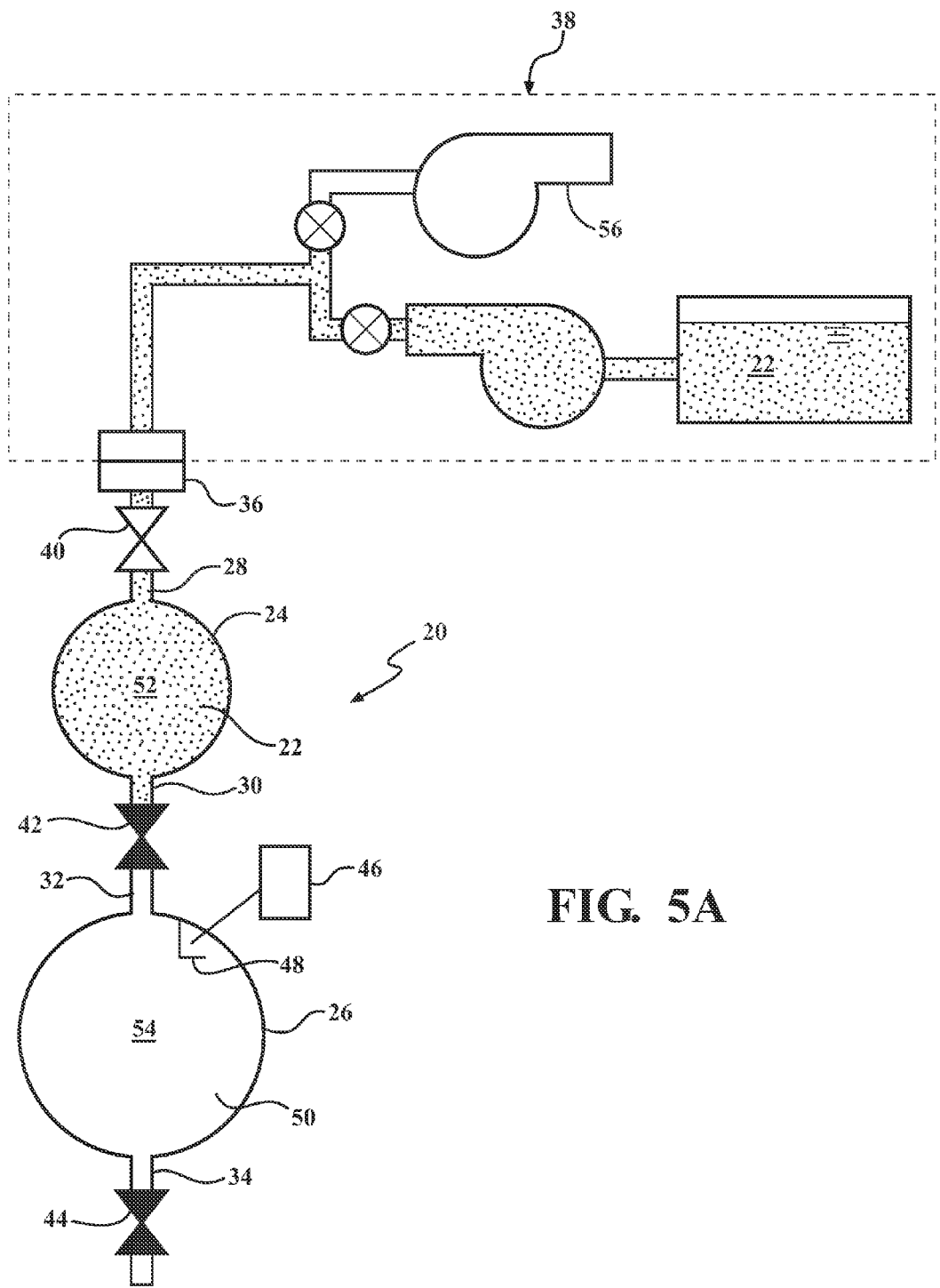
FIG. 5A is a schematic diagram of the fluid testing device showing a pressurized fluid being introduced into the first tank of the fluid testing device with the fluid evacuation and filling system.

Referring to FIG. 5A, after fluid communication between the first tank 24 and the second tank 26 is closed, fluid communication between the first tank 24 and the evacuation and fluid filling system 38 is opened to enable introduction of a test volume of the pressurized fluid 22 into the first tank 24. A portion of the supply volume of the pressurized fluid 22 is introduced into the first tank 24 through the evacuation and fluid filling system 38. The volume of the pressurized fluid 22 to be tested, hereinafter referred to as "the test volume", is approximately equal to the first volume 52 of the first tank 24, as the first tank 24 will be completely filled and pressurized until flow into the first tank 24 stops due to equalized pressure (the supply volume pressure becomes the same as the test volume pressure). The test volume of the pressurized fluid 22 may be introduced into the first tank 24 at a pressure between 30 psi and 150 psi, and at approximately any normal indoor ambient temperature suitable for production workers.

Figure 5B:
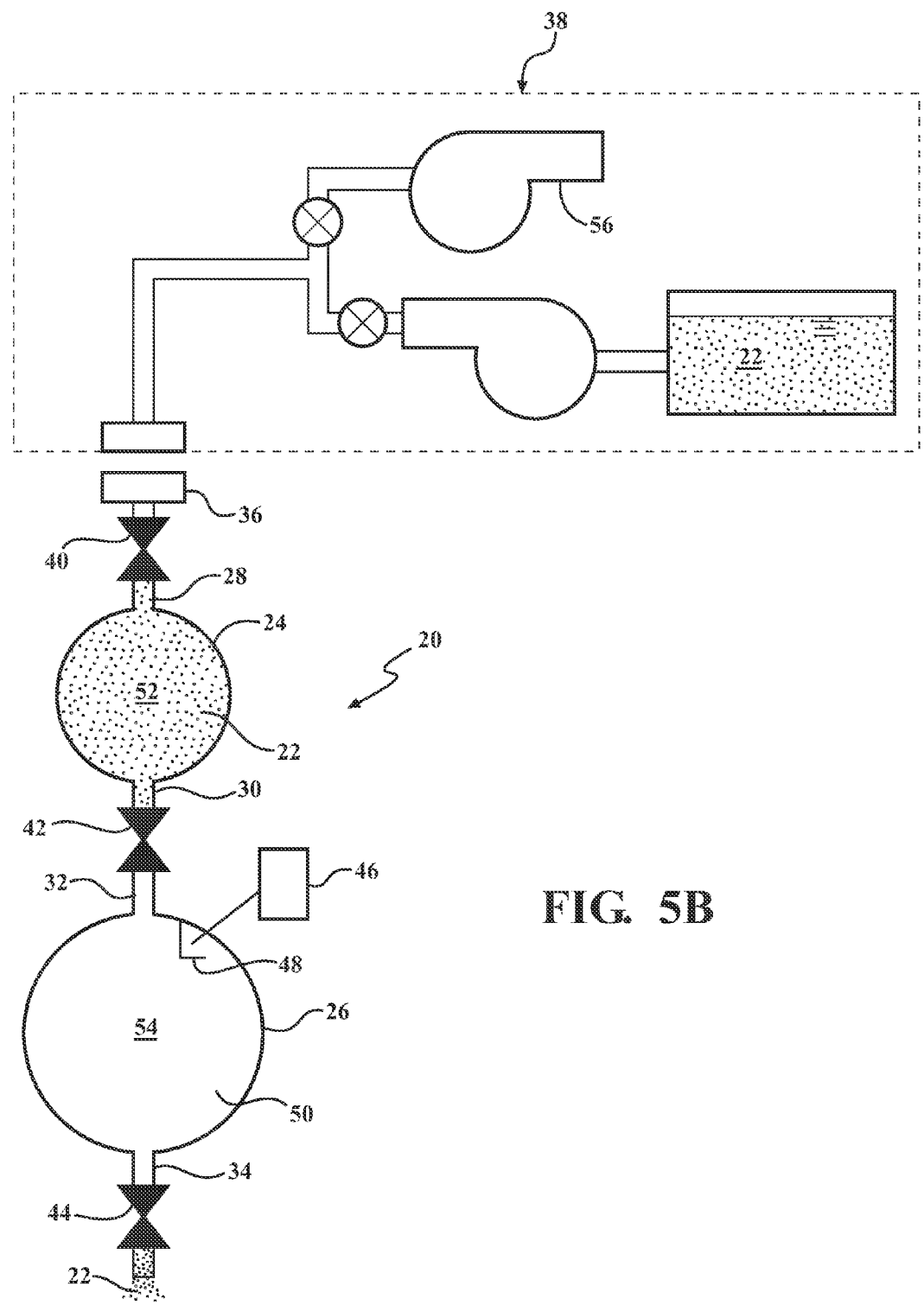
FIG. 5B is a schematic diagram of the fluid testing device showing the first tank filled with pressurized fluid, and the fluid evacuation and filling system de-coupled from the fluid testing device.

Referring to FIG. 5B, once the test volume of the pressurized fluid 22 is introduced into the first tank 24, fluid communication between the first tank 24 and the evacuation and fluid filling system 38 is closed, and the evacuation and fluid filling system 38 is disconnected from the first tank 24. Fluid communication between the first tank 24 and the evacuation and fluid filling system 38 is closed by moving the inlet valve 40 into its respective closed position. The evacuation and fluid filling system 38 is disconnected from the fluid testing device 20 by disengaging the fluid coupler 36.

After fluid communication between the first tank 24 and the evacuation and fluid filling system 38 has been closed, an initial absolute pressure in the second tank 26 is sensed with the absolute pressure sensor 46. The initial absolute pressure reading may be taken manually by an operator viewing the absolute pressure reading, or may be communicated to an electronic controller via an electric signal. The initial absolute pressure may be recorded, or saved in memory of an electronic controller for later use.

Figure 6:
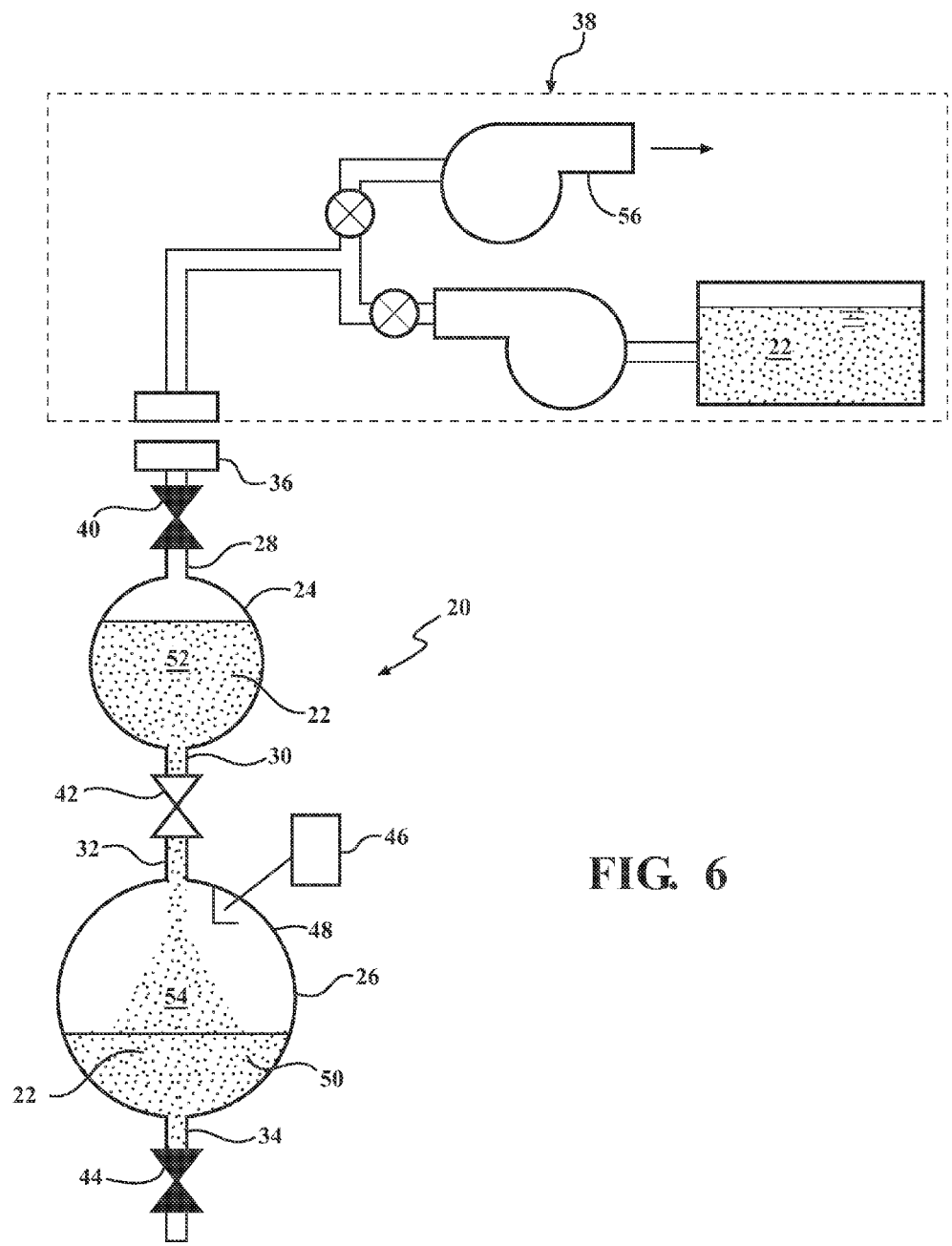
FIG. 6 is a schematic diagram of the fluid testing device showing the pressurized fluid flowing from the first tank into a second tank of the fluid testing device, and becoming a de-pressurized fluid as a result.

Referring to FIG. 6, after the initial absolute pressure is sensed with the absolute pressure sensor 46, fluid communication between the first tank 24 and the second tank 26 is opened to allow the test volume of the pressurized fluid 22 to flow from the first tank 24 into the second tank 26. Fluid communication between the first tank 24 and the second tank 26 is opened by moving the transfer valve 42 into its respective open position. As noted above, the first tank 24 is disposed vertically above the second tank 26 so that the test volume of the pressurized fluid 22 may flow by gravity from the first tank 24 into the second tank 26. Furthermore, because the transfer valve 42 was closed after forming the vacuum in both the first tank 24 and the second tank 26, and prior to introduction of the pressurized fluid 22 into the first tank 24, a vacuum exists in the second tank 26.

After the transfer valve 42 is opened to allow the pressurized fluid 22 to flow from the first tank 24 into the second tank 26, the fluid 22 de-pressurizes, and the test volume of the previously pressurized fluid 22 is maintained in the second tank 26 for a pre-defined out-gassing period, to allow any moisture and dissolved or entrained gasses in the test volume of the previously pressurized fluid 22 to separate from the liquid portion of the fluid 22 and to be measured by the change in reading of the absolute pressure sensor 46 at the end of the test process.

When the pressurized fluid 22 is introduced into the first tank 24, it is initially at a pressure that is significantly higher than the vacuum pressure in the second tank 26. At the higher pressure conditions (temperature assumed to be relatively constant throughout the test process), the liquid had allowed a solubility of a certain amount of air in that physical state. Air content beyond this level, if any, would not have been able to become dissolved and would have remained entrained in the liquid while under pressure. When the transfer valve 42 is opened the pressure of the first volume 52 of the fluid 22 in the first tank 24, being almost completely incompressible with exception of the minor amount of entrained air, if any, will almost instantly drop to the approximate vacuum level previously existing in the lower tank 26 (a near perfect vacuum). The level of this equalized pressure (both tank volumes and all matter within now being at one common absolute pressure) will almost immediately be an indication of the amount of entrained air that was in the liquid, which being less dense, will now have expanded into the void over the liquid level impacting the equalized pressure. Over the subsequent out-gassing time period, the dissolved air will now slowly come out of solution as well, with the assumption that a near perfect vacuum remains and was not significantly degraded by unusual quantities of entrained air. Note that the pressurized fluid 22, being properly processed initially, should have virtually no entrained air and that the vacuum level therefore should remain deep enough to cause the dissolved air outgassing of the liquid to proceed unabated. Note also that if enough air is entrained in the pressurized fluid 22 as delivered to the testing device 20 (a very large and unexpected amount), that the vacuum level resulting after equalization may be high enough to interfere with the complete removal of the dissolved gas in the liquid. In this case, the testing device 20 will still convey useful information that indicates this poor quality of processed fluid 22 and the need to address the issue prior to pursuing a more accurate and subsequent "dissolved air only" test should such a test be desired. Also, note that any indication of the existence of entrained air (by abnormally high equalization pressure for example), is also an indication that the level of dissolved air was at the saturation level for the physical conditions that existed when the pressurized fluid sample 22 was introduced into the testing device 20. The reason is that if any room for additional dissolved air had existed at those conditions, the entrained air would have dissolved into solution given some exposure time with the fluid at those conditions. So any evidence of entrained air measured is also an indication that the dissolved air level of the sample was saturated. All said then, the existence of entrained air does not invalidate the testing device 20 as a dissolved air detector and a distinction between the level of dissolved vs entrained gas present in the pressurized fluid test sample 22 is not critical to differentiate in order to derive meaning from the test results.

It is important to note that despite the difference in size of the first tank 24 as compared to the second tank 26, that the volume of physical space in the testing device 20, which is void of liquid prior to the transfer of the pressurized fluid from the first tank 24 into the second tank 26 remains the same as after the transfer (it is approximately equivalent to the volume of the first tank 26 in both cases). This being true, and considering the perfect gas law, the transfer itself will have no impact on the pressure of the fluid due to a change in volume which constrains any gas that may exist, or at some point come out of solution, internal to the test tool. Thus any change in measurable pressure is strictly due to the release of dissolved gas (entrained gas being absent as intended) from the liquid portion of the test sample. The reasoning for the second tank 26 being slightly larger than the first tank 24 is to allow some space which will be assured to be void of liquid fluid so that the absolute pressure sensor 46, being designed to measure the pressure of a gas volume, will not be submerged in liquid which may interfere with its ability to make a proper measurement. It should also be noted, again considering the perfect gas law, that the sensitivity of a pressure measurement, as impacted by the quantity of gas being removed from the liquid, will be directly impacted by the size of the space allowed for gas to accumulate. The size of this space is, in turn, determined by the relative difference in size between the two tanks. So a smaller difference in relative tank size will give more sensitivity/resolution of a pressure measurement. As a result, the first tank 25 and the second tank 26 should not be excessively different in size but only enough to assure proper operation of the absolute pressure sensor 46.

Another concept impacting measurability of the results is the absolute size of the two tanks 24, 26. If both tanks were to be larger, or both were smaller, for example, it would impact the amount of pressurized fluid 22 that could be tested, and as a result, the amount of dissolved gas that may potentially be produced by the test process. Thus a larger sample size may produce more gas which may produce a larger, more measurable difference in pressure as seen by the absolute pressure sensor 46. All said and done, once optimal absolute and relative tank sizes are determined, either empirically or in theory, it is critical to compare results from test to test with those sizes constant in order to get meaningful comparative test results with respect to the amount of dissolved air that existed in the pressurized fluid sample 22 presented for analysis.

Figure 7A:
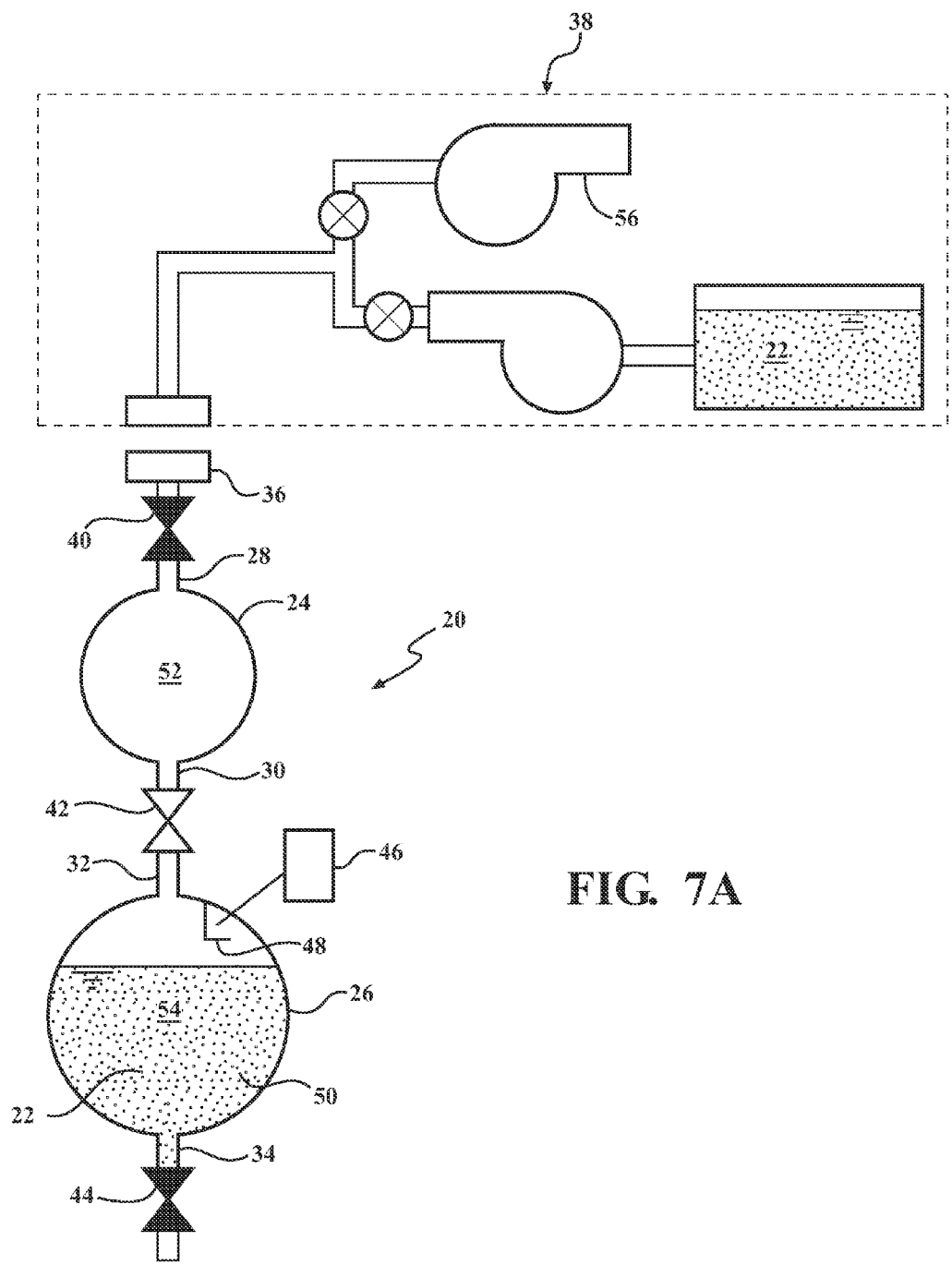
FIG. 7A is a schematic diagram of the fluid testing device showing the de-pressurized fluid settled to the bottom of the second tank, before gasses have separated from the de-pressurized fluid.

Referring to FIG. 7A, the de-pressurized fluid 22 is maintained in the second tank 26 for a pre-defined out-gassing period, to ensure that all dissolved gas has separated from the de-pressurized fluid 22. The pre-defined out-gassing period may include any time period required for the specific fluid being tested. For example, the pre-defined out-gassing period may be in the range of between 5 minutes and 20 minutes. However, the pre-defined out-gassing period may vary from the exemplary range provided herein.

Figure 7B:
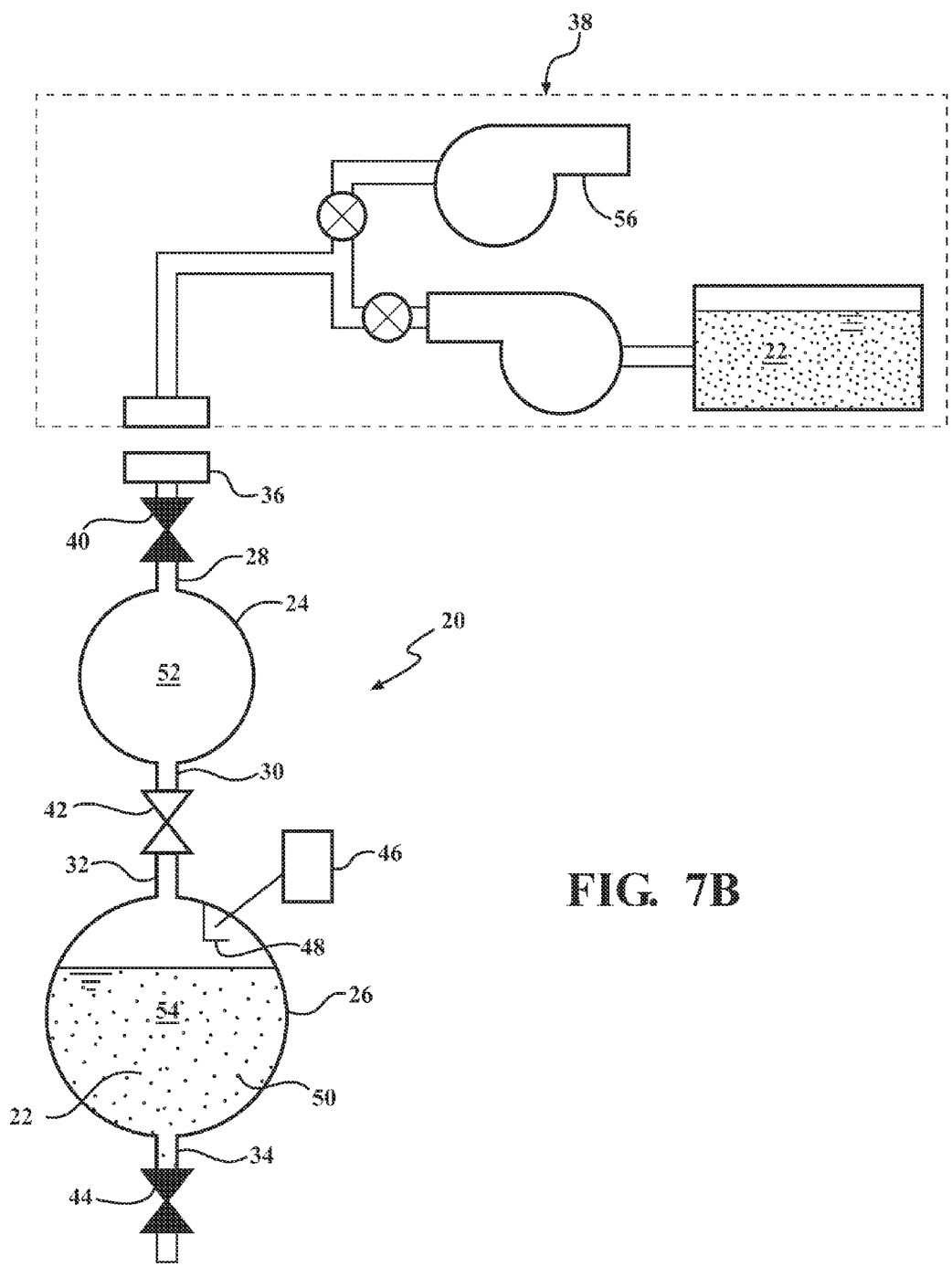
FIG. 7B is a schematic diagram of the fluid testing device showing the de-pressurized fluid settled to the bottom of the second tank, after gasses have separated from the de-pressurized fluid.

Referring to FIG. 7B, after the test volume of the pressurized fluid 22 has been maintained in the second tank 26 for the pre-defined out-gassing period, and the released gasses have collected at the top of the second tank 26, a final absolute pressure is sensed in the second tank 26 with the absolute pressure sensor 46. As noted above, a change in the absolute pressure in the second tank 26 is related to the separation of gasses and moisture from the pressurized fluid 22. A difference between the final absolute pressure and the initial absolute pressure may be calculated by subtracting the initial absolute pressure from the final absolute pressure. The difference between the final absolute pressure and the initial absolute pressure may then be correlated to a volume or quantity of gasses released from the test volume of the pressurized fluid 22. It should be noted that the pressurized fluid sample 22 may be so well processed prior to testing (extremely low or devoid of dissolved air) as to be called "super-processed" by some skilled in the art. A super-processed sample may actually lower the absolute pressure level in the second tank 26 when introduced to that tank because that pressure level may not be at zero absolute pressure initially (perfect evacuation is not actually feasible with the equipment used in automotive manufacturing, although the level gets very near perfect). So some amount of the residual air in the second tank 26, which remains prior to introduction of the fluid sample, can then be absorbed into solution (dissolved) by the super-processed fluid (the super-processed fluid not being saturated even at the very low pressure state that exists at this point) if such a well processed fluid is introduced. Thus the decay (final minus initial absolute pressure) may be negative thus indicating excellent super-processed fluid quality of the introduced sample. Note that a negative decay is not the same as a negative absolute pressure which is not physically possible, yet an end reading with a perfect vacuum (0.0 mmHg) can actually be achieved via this test method, and in theory, in a vehicle brake system. Any portion of the gasses released from the pressurized fluid 22 related to moisture in the fluid may be empirically correlated to an expected pressure change, based upon the boiling point of the fluid sample that was predetermined by independent known test methods applied to another sample from the same equipment which is being tested. Any increase in pressure over and above this value is attributed to dissolved gasses in the test sample.

Figure 8:
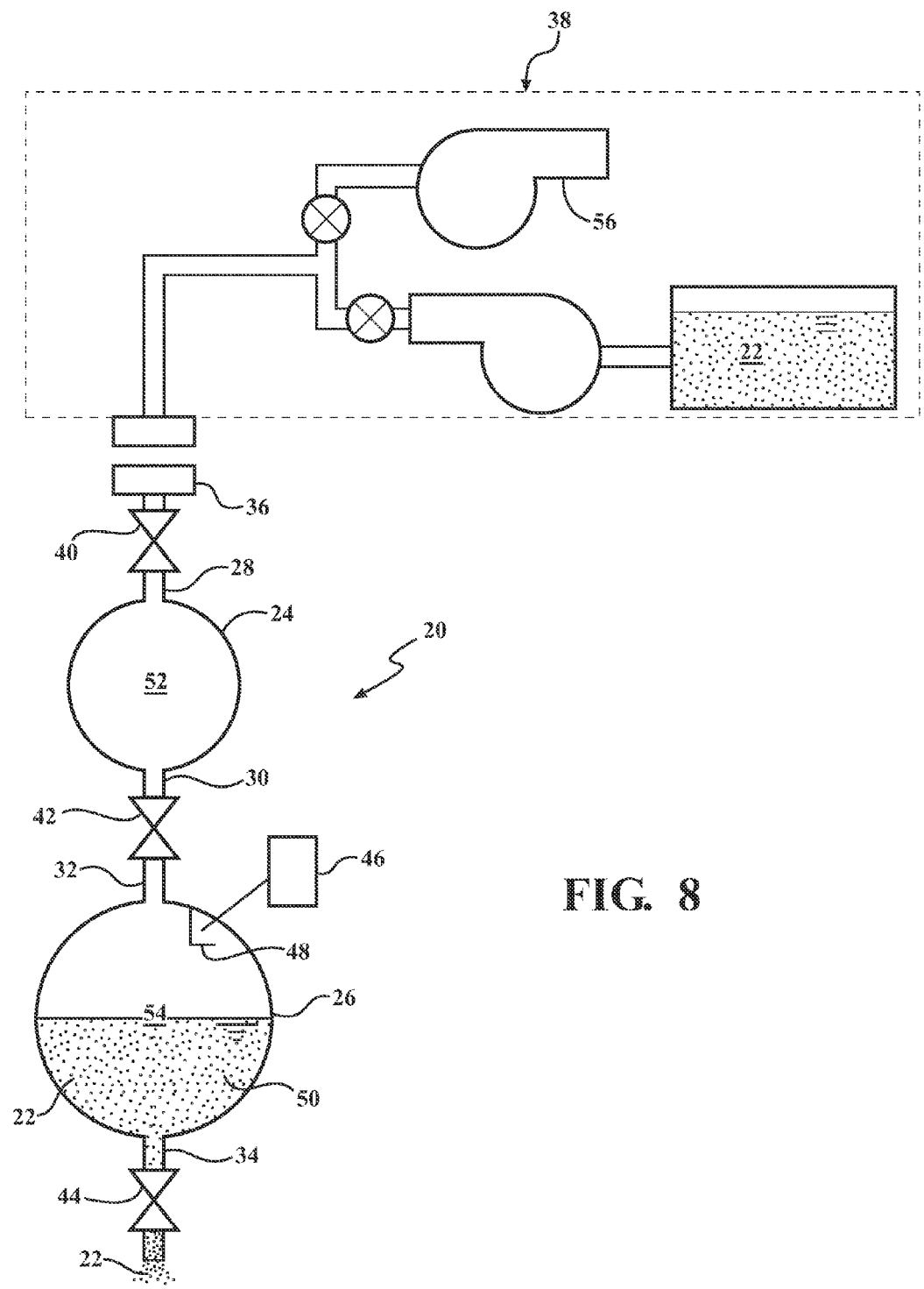
FIG. 8 is a schematic diagram of the fluid testing device showing the de-pressurized fluid being drained from the second tank.

Once the test is complete, and the change in pressure has been correlated to the volume of gasses in the test volume of the pressurized fluid 22, the drain valve 44 and the inlet valve 40 may be moved to their respective open positions, such as shown in FIG. 8, to allow fluid flow through the second outlet 34 of the second tank 26, in order to drain the test volume of the fluid 22 from the second tank 26. Some non-critical drain time may be allowed for draining the majority of the sample from the fluid testing device 20, although some residual fluid 22 may remain, and no rinsing of the fluid testing device 20 with a solvent is required. After the draining period, the fluid testing device 20 is returned to the storage position shown in FIG. 1, and described above.

The test results from the procedure described above, i.e., the volume or quantity of gas that was released from the test volume of the pressurized fluid 22 (as determined by the change in absolute pressure over the test period), may be tracked over time and/or used for several different purposes. For example, the test may be performed as a quality control to ensure that the fluid is being properly processed to remove the requisite amount of gas and/or moisture prior to installation into the hydraulic system. By tracking the test results over time, a malfunction in the processing or pressurized transport of the fluid may be detected. Furthermore, the test procedure may be used to compare different fluid processing techniques, to determine which technique is the most efficient at removing moisture and gasses from the fluid, and/or which is more cost effective. Alternatively, a malfunction in the evacuation performance of the evacuation and fluid filling system 38 may also be detected. For example, with minor modifications of the test process, the performance of the vacuum pump 56 of the evacuation and fluid filling system 38 may be tested.

A test of the evacuation performance of the evacuation and fluid filling system 38 would still require the pre-test outgassing step (including extended vacuum soak time for both tanks) in order to assure that moisture in the residual fluid in the fluid testing device 20 (from previous testing) would not influence the subsequent test results and also to assure that there is no leak in the fluid testing device 20 or leak in the interface between the evacuation and filling system 38 and the fluid testing device 20. For this testing of the evacuation performance of the fluid evacuation and filling system 38, after the pre-test outgassing, vacuum soak period and passing of the vacuum decay check, the first tank 24 would briefly be returned to atmospheric pressure, instead of proceeding directly to filling the first tank 24 without releasing the vacuum as described above. The second tank 26 would remain isolated form the first tank 24 and would remain under deep vacuum from the pre-test soak. At this point, the evacuation and filling test procedure described above may be performed using only the manufacturing production process vacuum evacuation period (in this case for the first tank only), thus testing the evacuation pumping capability to remove air to a very low absolute pressure very quickly as need in the manufacturing production environment.

Such a time period for the removal of air in the manufacturing environment may, for example, be in the range of 45 and 100 seconds. This manufacturing process is normally applied to a vehicle brake system that is expected to be very dry (no vacuum soak period should be needed, unlike the test fixture), as well as leak free via previous positive pressure leak checking of the system. As a result, the test fixture is both vacuum soaked and leak checked to simulate the condition of the vehicle system but then returned to atmospheric pressure conditions to enable testing of the ability of the evacuation and fill machine vacuum pump 56, to remove air efficiently and effectively in a limited amount of time (indicating normal operational capability). Any amount of air not fully removed in the allotted time will show up in the final test results, the same way that the dissolved gas test would show results, but in this case would primarily be an indication of vacuum pump performance.

The detailed description and the drawings or figures are supportive and descriptive of the disclosure, but the scope of the disclosure is defined solely by the claims. While some of the best modes and other embodiments for carrying out the claimed teachings have been described in detail, various alternative designs and embodiments exist for practicing the disclosure defined in the appended claims.

The invention claimed is:

1. A method of testing a pressurized fluid for dissolved and entrained gasses with a fluid testing device including a first tank having a first volume, and a second tank in fluid communication with the first tank and having a second volume that is larger than the first volume of the first tank, the method comprising:
   connecting an evacuation and fluid filling system to the first tank;
   evacuating both the first tank and the second tank with the evacuation and fluid filling system to form a vacuum in both the first tank and the second tank;
   blocking fluid communication between the first tank and the second tank;
   introducing a test volume of a pressurized fluid into the first tank with the evacuation and fluid filling system;
   preventing fluid communication between the first tank and the evacuation and fluid filling system;
   sensing an initial absolute pressure in the second tank with an absolute pressure sensor;
   opening fluid communication between the first tank and the second tank to allow the test volume of the pressurized fluid to flow from the first tank into the second tank, thereby de-pressurizing the test volume of the fluid;
   maintaining the test volume of the de-pressurized fluid in the second tank for a pre-defined out-gassing period to allow any dissolved or entrained gasses in the test volume of the de-pressurized fluid to separate from the de-pressurized fluid;
   sensing a final absolute pressure in the second tank with the absolute pressure sensor, after the test volume of the de-pressurized fluid has been maintained in the second tank for the pre-defined out-gassing period; and
   correlating a difference between the final absolute pressure and the initial absolute pressure to a volume of gasses released from the test volume of the de-pressurized fluid.

2. The method set forth in claim 1 further comprising opening fluid communication between the evacuation and fluid filling system and the first tank after connecting the evacuation and filling system to the first tank, and prior to evacuating the first tank and the second tank.

3. The method set forth in claim 2 further comprising blocking fluid communication between the evacuation and fluid filling system and the first tank after evacuating the first tank and the second tank, and prior to blocking fluid communication between the first tank and the second tank.

4. The method set forth in claim 3 further comprising maintaining the vacuum in both the first tank and the second tank for a pre-defined vacuum soak period to test for leaks in the fluid testing device, prior to blocking fluid communication between the first tank and the second tank.

5. The method set forth in claim 4 further comprising opening fluid communication between the first tank and the evacuation and fluid filling system after blocking fluid communication between the first tank and the second tank to enable the introduction of the test volume of the pressurized fluid into the first tank.

6. The method set forth in claim 5 further comprising disconnecting the evacuation and fluid filling system from the first tank after introducing the test volume of the pressurized fluid into the first tank and blocking fluid communication between the evacuation and fluid filling system and the first tank.

7. The method set forth in claim 6 further comprising calculating the difference between the final absolute pressure and the initial absolute pressure.

8. The method set forth in claim 7 wherein calculating the difference between the final absolute pressure and the initial absolute pressure includes subtracting the initial absolute pressure from the final absolute pressure.

9. The method set forth in claim 7 further comprising draining the test volume of the de-pressurized fluid from the second tank.

10. The method set forth in claim 1 wherein the test volume of pressurized fluid is brake fluid.

11. The method set forth in claim 10 wherein the test volume of pressurized fluid is introduced into the first tank at a pressure between 30 psi and 150 psi.

12. The method set forth in claim 1 wherein the first tank is disposed vertically above the second tank so that the test volume of the pressurized fluid flows by gravity from the first tank into the second tank, when fluid communication between the first tank and the second tank is opened.

13. A fluid testing device comprising:
   a first tank having a first inlet and a first outlet;
   a fluid coupler attached to the first inlet, and operable to connect the first inlet to an evacuation and fluid filling system;
   an inlet valve interconnecting the first inlet and the fluid coupler, and operable to open fluid communication between the first inlet and the fluid coupler, and block fluid communication between the first inlet and the fluid coupler;
   a second tank having a second inlet and a second outlet, wherein the second inlet is disposed in fluid communication with the first outlet of the first tank;
   a transfer valve interconnecting the first outlet of the first tank and the second inlet of the second tank, wherein the transfer valve is operable to open fluid communication between the first outlet and the second inlet, and block fluid communication between the first outlet and the second inlet;
   a drain valve attached to the second outlet, and operable to open fluid communication between the second outlet and atmospheric pressure, and block fluid communication between the second outlet and atmospheric pressure; and
   an absolute pressure sensor attached to the second tank, and operable to sense an absolute pressure within the second tank.

14. The fluid testing device set forth in claim 13 wherein the first tank defines a first volume, and the second tank defines a second volume, with the second volume larger than the first volume.

15. The fluid testing device set forth in claim 14 wherein the first volume and the second volume are each between 200 cc and 3000 cc.

16. The fluid testing device set forth in claim 14 wherein the second volume is between 2% and 50% larger than the first volume.

17. The fluid testing device set forth in claim 16 wherein the second volume is between 5% and 15% larger than the first volume.

18. The fluid testing device set forth in claim 13 wherein the first tank is disposed vertically above the second tank.

19. The fluid testing device set forth in claim 13 wherein the absolute pressure sensor is a digital sensor.

20. The fluid testing device set forth in claim 13 further comprising a baffle disposed within an interior of the second tank, and positioned to shield the absolute pressure sensor.

* * * * *